United States Patent
Nakagiri et al.

(10) Patent No.: US 7,138,386 B2
(45) Date of Patent: Nov. 21, 2006

(54) PREVENTIVES OR REMEDIES FOR ARTHRITIS

(75) Inventors: Ryusuke Nakagiri, Tsukuba (JP); Toshikazu Kamiya, Tsukuba (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/250,373

(22) PCT Filed: Dec. 27, 2001

(86) PCT No.: PCT/JP01/11541

§ 371 (c)(1),
(2), (4) Date: Jul. 1, 2003

(87) PCT Pub. No.: WO02/055074

PCT Pub. Date: Jul. 18, 2002

(65) Prior Publication Data

US 2004/0053884 A1    Mar. 18, 2004

(30) Foreign Application Priority Data

Jan. 5, 2001   (JP) ............................. 2001-300094
May 16, 2001   (JP) ............................. 2001-146465

(51) Int. Cl.
*A61K 31/715*   (2006.01)
*A61K 31/726*   (2006.01)
*A61K 31/70*    (2006.01)

(52) U.S. Cl. .................. 514/54; 514/62; 536/55.1; 536/55.2; 536/18.7; 536/54; 548/532

(58) Field of Classification Search .................. 514/54, 514/62; 536/55.1, 55.2, 18.7, 54; 548/532
See application file for complete search history.

(56) References Cited

FOREIGN PATENT DOCUMENTS

| | | |
|---|---|---|
| FR | 4727 M | 12/1967 |
| FR | 2 770 777 | 5/1999 |
| WO | 94/22453 | 10/1994 |
| WO | WO 99/62459 | 12/1999 |
| WO | 00/40217 | 7/2000 |
| WO | WO 00-40217 * | 7/2000 |

OTHER PUBLICATIONS

Mazieres et al. (J. Drug Dev. 1990:3(3) 135-142).*

Mazières, et al., "Effects of N-Acetyl Hydroxyproline (Oxaceprol) on an . . . ", J. Drug Dev., vol. 3, No. 3 (1990); pp. 135-142.

Kalbhen, et al., "Autoradiographic studies on the effect of oxaceprol on the metabolism of joint cartlilage *in virtro* and *in vivo*", Zeitschr. Rheumatol., 46,136-142(1987).

Riera, et al., *Revue du Rhumatsime*, vol. 58, No. 9 (1991), pp. 629-634.

* cited by examiner

*Primary Examiner*—Shaojia Anna Jiang
*Assistant Examiner*—Michael C. Henry
(74) *Attorney, Agent, or Firm*—Fitzpatrick, Cella, Harper & Scinto

(57) ABSTRACT

The present invention relates to pharmaceuticals, foods and drinks, food additives, animal feeds and feed additives comprising an N-acylated hydroxyproline derivative or a salt thereof, and an amino sugar or a salt thereof and/or a glycosaminoglycan or a salt thereof as active ingredients, use of an Nacylated hydroxyproline derivative or a salt thereof for the production of an arthritis preventing or treating agent, and a method for preventing or treating arthritis which comprises administering an N-acylated hydroxyproline derivative or a salt thereof, and an amino sugar or a salt thereof and/or a glycosaminoglycan or a salt thereof.

19 Claims, No Drawings

PREVENTIVES OR REMEDIES FOR ARTHRITIS

TECHNICAL FIELD

The present invention relates to pharmaceuticals, foods and drinks, food additives, animal feeds and feed additives having an effect on the prevention or the treatment of arthritis.

BACKGROUND ART

With changes in our lifestyle and aging of the population, arthritis is expected to increase in the future.

N-Acetylhydroxyproline is known as a chemical substance that shows anti-inflammatory activity (U.S. Pat. Nos. 3,891,765 and 3,932,638; Japanese Published Examined Patent Application No. 43947/72).

It is known that administration of N-acetylhydroxyproline to an animal model for arthritis after induction of arthritis can prevent aggravation of arthritis [J. Drug. Dev., 3, 135–142 (1990)]. It is also known that although N-acetylhydroxyproline shows a therapeutic effect on systemic injury of ear and tail, it shows no effect on chondral injury at joints [Pharmacological Research, 33, 367–373 (1996)].

However, it has not been known so far that N-acylated hydroxyproline derivatives such as N-acetylhydroxyproline show a preventive effect on arthritis.

Furthermore, although chondroitin, glucosamine, etc. that are the components of cartilages are known to have a therapeutic effect on arthritis (WO94/22453), there has not been known a composition obtained by the addition of an N-acylated hydroxyproline derivative thereto.

DISCLOSURE OF THE INVENTION

An object of the present invention is to provide a pharmaceutical, a food and drink, a food additive, an animal feed and a feed additive having an effect on the prevention or the treatment of arthritis and a method for preventing or treating arthritis in humans or non-human animals using them.

The present invention relates to the following (1)–(22).

(1) A pharmaceutical which comprises an N-acylated hydroxyproline derivative or a salt thereof, and an amino sugar or a salt thereof and/or a glycosaminoglycan or a salt thereof.

(2) The pharmaceutical according to the above (1), wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

(3) The pharmaceutical according to the above (1) or (2), wherein the acyl moiety of said N-acylated hydroxyproline derivative is an acyl group having 2–23 carbon atoms.

(4) The pharmaceutical according to any one of the above (1) to (3), wherein said N-acylated hydroxyproline derivative is N-acetylhydroxyproline.

(5) The pharmaceutical according to any one of the above (1) to (4), wherein said amino sugar is glucosamine or a salt thereof.

(6) The pharmaceutical according to any one of the above (1) to (5), wherein said glycosaminoglycan is chondroitin sulfate or a salt thereof.

(7) The pharmaceutical according to any one of the above (1) to (6), wherein said pharmaceutical is a pharmaceutical for preventing or treating arthritis.

(8) The pharmaceutical according to the above (7), wherein said arthritis is rheumatoid arthritis.

(9) A food and drink or an animal feed which comprises an N-acylated hydroxyproline derivative or a salt thereof, and an amino sugar or a salt thereof and/or a glycosaminoglycan or a salt thereof.

(10) The food and drink or the animal feed according to the above (9), wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

(11) The food and drink or the animal feed according to the above (9) or (10), wherein the acyl moiety of said N-acylated hydroxyproline derivative is an acyl group having 2–23 carbon atoms.

(12) The food and drink or the animal feed according to any one of the above (9) to (11), wherein said N-acylated hydroxyproline derivative is N-acetylhydroxyproline.

(13) The food and drink or the animal feed according to any one of the above (9) to (12), wherein said amino sugar is glucosamine or a salt thereof.

(14) The food and drink or the animal feed according to any one of the above (9) to (13), wherein said glycosaminoglycan is chondroitin sulfate or a salt thereof.

(15) A food additive or a feed additive which comprises an N-acylated hydroxyproline derivative or a salt thereof, and an amino sugar or a salt thereof and/or a glycosaminoglycan or a salt thereof.

(16) The food additive or the feed additive according to the above (15), wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

(17) The food additive or the feed additive according to the above (15) or (16), wherein the acyl moiety of said N-acylated hydroxyproline derivative is an acyl group having 2–23 carbon atoms.

(18) The food additive or the feed additive according to any one of the above (15) to (17), wherein said N-acylated hydroxyproline derivative is N-acetylhydroxyproline.

(19) The food additive or the feed additive according to any one of the above (15) to (18), wherein said amino sugar is glucosamine or a salt thereof.

(20) The food additive or the feed additive according to any one of the above (15) to (19), wherein said glycosaminoglycan is chondroitin sulfate or a salt thereof.

(21) Use of an N-acylated hydroxyproline derivative or a salt thereof, and an amino sugar or a salt thereof and/or a glycosaminoglycan or a salt thereof for the production of an arthritis preventing or treating agent.

(22) A method for preventing or treating arthritis in humans or non-human animals, which comprises administering an N-acylated hydroxyproline derivative or a salt thereof, and an amino sugar or a salt thereof and/or a glycosaminoglycan or a salt thereof.

Hydroxyproline widely occurs in nature as a major amino acid component of collagen and as an amino acid component of elastin. It is known that there exist eight kinds of stereoisomers of natural hydroxyproline, which are distinct in the following points: proline is the D-form or the L-form, the hydroxyl group is at the 3-position or the 4-position, and the stereoisomer is the cis-form or the trans-form, examples thereof being cis-4-hydroxy-L-proline, cis-4-hydroxy-D- proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

Although hydroxyproline of any such structure can be used in the present invention, trans-4-hydroxy-L-proline is preferably used.

Hydroxyproline can be obtained by subjecting collagen derived from animals such as pig and cow to acid hydrolysis and purifying the hydrolysate according to a conventional method. However, hydroxyproline produced using microorganisms is preferably used.

Useful microorganisms include those belonging to the genus selected from *Amycolatopsis, Dactylosporangium* and *Streptomyces* or those into which a proline 3-hydroxylase gene or a proline 4-hydroxylase gene derived from these microorganisms has been introduced.

Introduction of a proline 3-hydroxylase gene or a proline 4-hydroxylase gene derived from a microorganism belonging to the genus selected from *Amycolatopsis, Dactylosporangium* and *Streptomyces* into a microorganism can be carried out according to the methods described in Molecular Cloning, A Laboratory Manual, Second Edition, Cold Spring Harbor Laboratory Press (1989), Current Protocols in Molecular Biology, John Wiley & Sons (1987–1997), etc.

Furthermore, trans-4-hydroxy-L-proline can be produced using proline 4-hydroxylase isolated from a microorganism belonging to the genus *Amycolatopsis* or *Dactylosporangium* (Japanese Published Unexamined Patent Application No. 313179/95), and cis-3-hydroxy-L-proline can be produced using proline 3-hydroxylase isolated from a microorganism belonging to the genus *Streptomyces* (Japanese Published Unexamined Patent Application No. 322885/95) [Bioindustry, 14, 31 (1997)].

The acyl moiety of the N-acylated hydroxyproline derivatives used in the present invention includes straight-chain or branched acyl groups having 2–23 carbon atoms, for example, acetyl, propionyl, butyryl, isobutyryl, valeryl, hexanoyl, heptanoyl, octanoyl, decanoyl and eicosanoyl, among which acetyl and propionyl are preferred.

The N-acylated hydroxyproline derivatives can be produced according to a known method.

That is, the N-acylated hydroxyproline derivatives can be prepared by N-acylating hydroxyproline in an aqueous medium or an organic solvent using an active derivative (acid anhydride, acid chloride, etc.) of a fatty acid having an alkyl group having preferably 1–22 carbon atoms.

The N-acylated hydroxyproline derivatives thus obtained can be purified by conventional purification methods such as crystallization and chromatography.

Examples of the salts of N-acylated hydroxyproline derivatives include alkali metal salts such as sodium salt and potassium salt, alkaline earth metal salts such as magnesium salt and calcium salt, ammonium salts such as ammonium salt and tetramethylammonium salt, and organic amine addition salts such as salts with morpholine and piperidine.

In the present invention, examples of the amino sugars or salts thereof are glucosamine, galactosamine, neuraminic acid, N-acetylglucosamine, N-acetylgalactosamine, N-acetylneuraminic acid and N-glycolyl-neuraminic acid or salts thereof. Glucosamine or salts thereof are preferably used. Examples of the salts of amino sugars are hydrochloride, sulfate and phosphate.

Glucosamine obtained, for example, by hydrolyzing, with concentrated hydrochloric acid, chitin obtained by deproteinizing and decalcifying shells of crustacean and then deacetylating, bleaching, filtering, concentrating, separating, washing and drying the hydrolysate may be used. Otherwise, commercially available products (for example, Glucosamine KHF: KYOWA HI FOODS CO., LTD.) may also be used.

Examples of the salts of glucosamine are hydrochloride, sulfate (for example, glucosamine hexasulfate) and phosphate (for example, glucosamine hexaphosphate).

Galactosamine obtained, for example, by subjecting chondroitin sulfate prepared from cartilages of bronchus, nose, etc. of large animals and cartilages of selachian to acid hydrolysis and separating and purifying the resulting hydrolysate according to methods such as ion exchange chromatography may be used. Otherwise, commercially available products may also be used.

Examples of the salts of galactosamine are hydrochloride, sulfate (for example, galactosamine hexasulfate) and phosphate (for example, galactosamine hexaphosphate).

Neuraminic acid commercially available as N-acetyl-neuraminic acid which is an N-acylated derivative thereof and N-glycolyl-neuraminic acid which is an N-glycolyl derivative thereof may be used.

In the present invention, the glycosaminoglycans include hyaluronic acid, chondroitin, chondroitin sulfate, keratan sulfate, heparin, heparan sulfate and dermatan sulfate and salts thereof, and chondroitin sulfate or salts thereof are preferably used.

Examples of the salts of glycosaminoglycans are sodium salt, potassium salt and calcium salt.

Examples of the salts of chondroitin sulfate are sodium salt, potassium salt and calcium salt, and sodium salt is generally used.

Chondroitin sulfate is a kind of mucopolysaccharides that are generally distributed in connective tissues of animals, mainly in cartilages. In the tissues, this substance connects with protein to occur as proteoglycan.

Chondroitin sulfate to be used may be either in the form of a purified product or in the form of proteoglycan, or an extract or a dry powder of cartilages.

Chondroitin sulfate can be obtained in the form of proteoglycan by, for example, subjecting cartilages of aquatic animals such as shark and whale, mammals such as cow and pig or birds as a raw material to extraction according to known methods such as neutral salt method, alkaline method, enzymatic method and autoclave method, and drying the extract after removing fat and solid content therefrom. Furthermore, after removal of fat and solid content, chondroitin sulfate or a salt thereof can be obtained in a purified form by deproteonizing the resulting extract using a protease and purifying the protein-free extract according to a known method using alcohol precipitation.

As the glycosaminoglycans and salts thereof, commercially available hyaluronic acid, chondroitin, chondroitin sulfate, chondroitin hydrochloride, keratan sulfate, heparin, heparan sulfate and dermatan sulfate or salts thereof may also be used.

The pharmaceuticals, the foods and drinks, the animal feeds, the food additives and the feed additives of the present invention, and the method for preventing or treating arthritis in humans or non-human animals using them are described below.

The present invention can be applied to any arthritis including chlamydial arthritis, chronic absorptive arthritis, enteropathic arthritis, gonococcal arthritis, gouty arthritis, Jaccoud arthritis, juvenile arthritis, Lyme arthritis, ochronotic arthritis, suppurative arthritis, osteoarthritis, periarthritis scapulohumeralis (so-called frozen shoulder), arthritis caused by excessive work load and rheumatoid arthritis, and is particularly advantageous to rheumatoid arthritis.

(a) a Pharmaceutical comprising N-acylated hydroxyproline derivative or salt thereof, and amino sugar or salt thereof and/or glycosaminoglycan or salt thereof as active ingredients, and method for preventing or treating arthritis in humans or non-human animals using the pharmaceutical The pharmaceutical of the present invention includes any pharmaceuticals that comprise the N-acylated hydroxyproline derivative or a salt thereof, and the amino sugar or a salt thereof and/or the glycosaminoglycan or a salt thereof as active ingredients. They are preferably used as an arthritis preventing or treating agent.

In addition to the N-acylated hydroxyproline derivative or a salt thereof, and the amino sugar or a salt thereof and/or the glycosaminoglycan or a salt thereof, the pharmaceutical of the present invention may also comprise other optional ingredients that are effective in preventing or treating arthritis.

Examples of the other ingredients that are effective in preventing or treating arthritis (hereinafter also referred to simply as "other active ingredients") are purified products or extracts of, or products containing boron, calcium, chromium, copper, magnesium, manganese, selenium, silicone, zinc, S-adenosyl methionine, collagen, collagen hydrolysate, gelatin, gelatin hydrolysate, bromelain, trypsin, chymotrypsin, papain, rutin, carotenoid, flavonoid, antioxidant vitamins, γ-linolenic acid, eicosapentaenoic acid, boswellia, capsaicin, cat's claw, devil's claw, fever few, ginger, nettles, niacinamide, shark cartilage, turmeric, curcumin, and the like.

The pharmaceutical of the present invention is produced by optional methods well known in the technical field of pharmaceutics by mixing the N-acylated hydroxyproline derivative or a salt thereof, and the amino sugar or a salt thereof and/or the glycosaminoglycan or a salt thereof as well as other active ingredients as required together with one or more pharmaceutically acceptable carriers.

In administering the pharmaceutical of the present invention, it is desirable to select a route of administration that is effective in the prevention or the treatment of arthritis, examples thereof being oral administration and parenteral administrations such as intravenous administration.

Examples of the dosage form are tablets, capsules, injections, drops, syrups, sublingual tablets, various types of creams and suppositories.

Liquid preparations such as syrups that are suitable for oral administration can be produced using water, sugars such as sucrose, sorbitol and fructose, glycols such as polyethylene glycol and propylene glycol, oils such as sesame oil, olive oil and soybean oil, antiseptics such as p-hydroxybenzoic acid esters, flavors such as strawberry flavor and peppermint, etc. Furthermore, tablets, powders and granules can be produced using excipients such as lactose, glucose, sucrose and mannitol, disintegrators such as starch and sodium alginate, lubricants such as magnesium stearate and talc, binders such as polyvinyl alcohol, hydroxypropyl cellulose and gelatin, surfactants such as fatty acid esters, plasticizers such as glycerin, etc.

Preparations appropriate for parenteral administration comprise, preferably, a sterilized aqueous agent containing an active compound, which is isotonic to the recipient's blood. In the case of an injection, for example, an injectable solution is prepared using a carrier consisting of a salt solution, a glucose solution or a mixture of saline and a glucose solution.

In producing these parenteral preparations, it is also possible to add one or more supplementary components selected from diluents, antiseptics, flavors, excipients, disintegrators, lubricants, binders, surfactants, plasticizers and the like exemplified in connection with oral preparations.

The content of the N-acylated hydroxyploline derivative or a salt thereof in the pharmaceutical of the present invention is 1–1000 mg/g, preferably 10–500 mg/g, especially preferably 100–200 mg/g of the pharmaceutical.

The content of the amino sugar or a salt thereof and the glycosaminoglycan or a salt thereof in the pharmaceutical of the present invention is not restricted so far as at least either of them is contained in an amount of 1–1000 mg/g, preferably 10–500 mg/g, especially preferably 100–200 mg/g of the pharmaceutical.

The composition ratio of the N-acylated hydroxyproline derivative or a salt thereof to the amino sugar or a salt thereof and/or the glycosaminoglycan or a salt thereof in the pharmaceutical of the present invention is 1:100–100:1, preferably 1:50–50:1, especially preferably 10:1–1:10 in terms of weight ratio.

The dosage and the frequency of administration of the pharmaceutical of the present invention vary depending on the mode of administration, the age, the body weight and the symptoms of the patient.

In the case of oral administration, the pharmaceutical is administered in a dose of 1–5000 mg, preferably 10–1000 mg, especially preferably 100–500 mg as N-acylated hydroxyproline derivative or salt thereof and amino sugar or salt thereof and/or glycosaminoglycan or salt thereof, respectively, per adult person once to several times a day.

In the case of parenteral administration such as intravenous administration, the pharmaceutical is administered in a dose of 0.5–5000 mg, preferably 5–1000 mg, especially preferably 50–500 mg as N-acylated hydroxyproline derivative or salt thereof, and amino sugar or salt thereof and/or glycosaminoglycan or salt thereof, respectively, per adult person once to several times a day.

By administering the pharmaceutical of the present invention on a daily basis, it is possible to prevent arthritis.

When arthritis has already been developed, it is possible to treat it by administering the pharmaceutical on a daily basis. The dosing period is usually one week to 10 years, preferably one month to 5 years.

The term "to prevent arthritis" as used herein means bringing about an effect of completely preventing the development of arthritis, reducing the incidence or suppressing the symptoms at the time of the onset by ingesting the foods and drinks, animal feeds, food additives or feed additives to be explained in (b) below or the above-described pharmaceutical on a daily basis.

On the other hand, the term "to treat arthritis" as used herein means bringing about an effect of relieving or treating the symptoms by administering the above-described pharmaceutical after the onset of arthritis.

The pharmaceutical of the present invention can be used not only for humans but also for animals other than humans (non-human animals). When used for non-human animals, the dose is 0.02–100 mg/kg, preferably 0.2–20 mg/kg, especially preferably 2–10 mg/kg of the body weight of the non-human animal to which the pharmaceutical is administered as N-acylated hydroxyproline derivative or salt thereof, and amino sugar or salt thereof and/or glycosaminoglycan or salt thereof, respectively.

The active ingredients of the above pharmaceutical are not necessarily administered simultaneously so far as they are administered within the period for which each of them has an effect.

Furthermore, the above pharmaceutical may be prepared so that the N-acylated hydroxyproline derivative or a salt thereof, and the amino sugar or a salt thereof and/or the glycosaminoglycan or a salt thereof are contained in the same preparation. It may also be prepared as a preparation in the form of a kit.

The preparation in the form of a kit (hereinafter referred to simply as "a kit") as used herein means two or more preparations prepared according to a conventional method by mixing a substance or a combination of substances selected from the N-acylated hydroxyproline derivatives or salts thereof, the amino sugars or salts thereof and the glycosaminoglycans or salts thereof with one or more pharmaceutically acceptable carriers, any of which comprises the N-acylated hydroxyproline derivative or a salt thereof as an active ingredient.

Examples of the combination of preparations constituting the kit are a combination of a preparation comprising the N-acylated hydroxyproline derivative or a salt thereof and a preparation comprising the amino sugar or a salt thereof; a combination of a preparation comprising the N-acylated hydroxyproline derivative or a salt thereof and a preparation comprising the glycosaminoglycan or a salt thereof; a combination of a preparation comprising the N-acylated hydroxyproline derivative or a salt thereof, a preparation comprising the amino sugar or a salt thereof and a preparation comprising the glycosaminoglycan or a salt thereof; and a combination of a preparation comprising the N-acylated hydroxyproline derivative or a salt thereof and a preparation comprising the amino sugar or a salt thereof and the glycosaminoglycan or a salt thereof, although the combination is not limited thereto.

Each of the preparations included in the kit may be in any form so long as they exist separately. For example, they may be packed separately or may be present as a mixture in the same vial.

In administering the preparations in the form of a kit, they may be administered either simultaneously or separately.

When administered separately, it is desirable that the preparations are administered within the period during which the active ingredients contained in the preparations are highly effective in a body. For example, all preparations are administered within 8 hours, preferably within 2 hours per one administration.

For the kit-form preparations, the dose is set so that the total dose per day of each active ingredient in the preparations corresponds to the above-described daily dose of each ingredient.

(b) Foods and drinks, animal feeds, food additives and feed additives comprising N-acylated hydroxyproline derivative or a salt thereof, and amino sugar or a salt thereof and/or glycosaminoglycan or a salt thereof, and method for preventing or treating arthritis in humans or non-human animals using them The foods and drinks of the present invention are obtained by adding the N-acylated hydroxyproline derivative or a salt thereof, and the amino sugar or a salt thereof and/or the glycosaminoglycan or a salt thereof to foods and drinks.

The foods and drinks of the present invention also include those obtained by the addition of the food additives of the present invention.

The foods and drinks of the present invention further include those obtained by adding other active ingredients described in (a) above in addition to the N-acylated hydroxyproline derivative or a salt thereof, and the amino sugar or a salt thereof and/or the glycosaminoglycan or a salt thereof.

Except the addition of the N-acylated hydroxyproline derivative or a salt thereof, and the amino sugar or a salt thereof and/or the glycosaminoglycan or a salt thereof, or other active ingredients as required, the foods and drinks of the present invention can be produced using a process generally used for producing foods and drinks.

The foods and drinks of the present invention may be in any of the forms including juice, soft drinks, tea, lactic acid beverages, fermented milk, ices, dairy products such as butter, cheese, yogurt, processed milk and skim milk, meat products such as ham, sausages and hamburger, fish products such as steamed, baked or fried fish paste, egg products such as baked or steamed foods made of beaten eggs, confectionery such as cookies, jellies, chewing gum, candies and snacks, bread, noodles, pickles, smoked foods, dried fish, preserved foods boiled down in soy sauce, salted foods, soups and seasonings.

Furthermore, the foods and drinks of the present invention may take the form of a powdered food, a sheet-shaped food, a bottled food, a canned food, a retort food, a capsule food, a tablet food, a liquid food, a health drink, etc.

The foods and drinks of the present invention can be used as a health food or a functional food having an effect on the prevention or treatment of arthritis.

When the foods and drinks of the present invention are a drink or a tablet, for example, they can be prepared by adding, to the N-acylated hydroxyproline derivative or a salt thereof, and the amino sugar or a salt thereof and/or the glycosaminoglycan or a salt thereof, other active ingredients, additives, etc. as required and then dissolving or dispersing the mixture in an appropriate amount of water or tableting the mixture. Furthermore, when the foods and drinks of the present invention are confectionary such as caramels, drops, chocolate, jelly, biscuits and cookies, they can be prepared by adding, to the N-acylated hydroxyproline derivative or a salt thereof, and the amino sugar or a salt thereof and/or the glycosaminoglycan or a salt thereof, other active ingredients, additives, etc. as required and additionally appropriate carriers such as wheat flour, rice flour, starch, corn starch, soybean, etc. as required and shaping the obtained mixture into an appropriate form according to a conventional method.

The foods and drinks of the present invention can also be produced by using granulating methods such as fluidized bed granulation, stirring granulation, extrusion granulation, rolling granulation, air stream granulation, compression molding granulation, disruption granulation, spray granulation and blasting granulation, coating methods such as pan coating, fluidized bed coating and dry coating, plumping methods such as puff drying, excess steam method, foam mat method and microwave heating method, and extrusion methods using an extruding granulator or an extruder.

The food additives of the present invention can be prepared according to methods similar to those mentioned in (a) above with respect to oral preparations. They can be produced, for example, into powder, granules, pellets, tablets and various liquid preparations by mixing with or dissolving together with other food additives as required.

To the foods and drinks or food additives of the present invention may be added food additives generally employed in foods and drinks such as sweeteners, coloring agents, preservatives, thickening stabilizers, antioxidants, color developing agents, bleaching agents, fungicides, gum bases, bittering agents, enzymes, glazing agents, acidulants, seasonings, emulsifiers, nutrient supplements, additional materials for preparation, flavors and spice extracts.

To the foods and drinks of the present invention, the N-acylated hydroxyproline derivative or a salt thereof, and the amino sugar or a salt thereof and/or the glycosaminoglycan or a salt thereof are added so that they are ingested generally in an amount of 1–5000 mg, preferably 10–1000 mg, especially preferably 100–500 mg per adult person per day, respectively, although the amount may vary depending upon the form of the foods and drinks.

These foods and drinks may be ingested once or in several divided parts a day.

The composition ratio of the N-acylated hydroxyproline derivative or a salt thereof to the amino sugar or a salt thereof and/or the glycosaminoglycan or a salt thereof in the foods and drinks of the present invention is 1:100–100:1, preferably 1:50–50:1, especially preferably 10:1–1:10 in terms of weight ratio.

The period of ingestion is usually one week to 10 years, preferably one month to 5 years.

As in the case of the pharmaceutical of the present invention, the foods and drinks of the present invention may be produced so that the N-acylated hydroxyproline derivative or a salt thereof, and the amino sugar or a salt thereof and/or the glycosaminoglycan or a salt thereof are contained in the same food and drink, or may be prepared as a set of foods and drinks.

Examples of the combination of the set of foods and drinks are a combination of a food and drink comprising the N-acylated hydroxyproline derivative or a salt thereof and a food and drink comprising the amino sugar or a salt thereof; a combination of a food and drink comprising the N-acylated hydroxyproline derivative or a salt thereof and a food and drink comprising the glycosaminoglycan or a salt thereof; a combination of a food and drink comprising the N-acylated hydroxyproline derivative or a salt thereof, a food and drink comprising the amino sugar or a salt thereof and a food and drink comprising the glycosaminoglycan or a salt thereof; and a combination of a food and drink comprising the N-acylated hydroxyproline derivative or a salt thereof and a food and drink comprising the amino sugar or a salt thereof and the glycosaminoglycan or a salt thereof, although the combination is not limited thereto.

Each of the foods and drinks included in the set may be in any form so long as they exist separately. For example, they may be packed separately or may be present as a mixture in the same container.

In ingesting the set of the foods and drinks, they may be ingested either simultaneously or separately.

When separately ingested, it is desirable that the foods and drinks are ingested within the period during which the active ingredients contained in the foods and drinks are highly effective in a body. For example, all foods and drinks are ingested within 8 hours, preferably within 2 hours per one intake.

The intake of the foods and drinks is set so that the total intake per day of each active ingredient in the foods and drinks corresponds to the above-described daily intake of each ingredient.

The animal feeds of the present invention comprise an animal feed to which the N-acylated hydroxyproline derivative or a salt thereof, and the amino sugar or a salt thereof and/or the glycosaminoglycan or a salt thereof are added. If necessary, the other active ingredients described in (a) above may also be added thereto.

The animal feeds of the present invention include any feeds that prevent or treat arthritis in non-human animals, preferably vertebrates, such as mammals other than humans, birds, reptiles, amphibians and fish, examples thereof being feeds for pets such as dogs, cats, rabbits and mice, pet food, feeds for livestock such as cows and pigs, feeds for poultry such as hens and turkeys, feeds for reptiles such as lizards, crocodiles and iguanas, feeds for amphibians such as frogs and newts and feeds for cultivated fish such as sea breams and young yellowtails.

The animal feeds of the present invention can be used as health supplement feeds for animals having an effect on the prevention or the treatment of arthritis.

Except the addition of the N-acylated hydroxyproline derivative or a salt thereof, and the amino sugar or a salt thereof and/or the glycosaminoglycan or a salt thereof, and additionally other active ingredients, if necessary, or the feed additive of the present invention to a feed, the animal feeds of the present invention can be produced using a process generally used for producing feeds.

The feeds include grains, bran, vegetable oil cakes, animal-based feed, other feeds and purified products, or mixtures thereof.

Examples of the grains are milo, wheat, barley, oats, rye, brown rice, buckwheat, foxtail millet, broomcorn millet, Japanese millet, corn and soybean.

Examples of the bran are rice bran, defatted rice bran, wheat bran, wheat middlings, wheat, germ, barley bran, pellet, corn bran and corn germ.

Examples of the vegetable oil cakes are soybean oil cake, soybean flour, linseed oil cake, cottonseed oil cake, peanut oil cake, safflower oil cake, coconut oil cake, palm oil cake, sesame oil cake, sunflower oil cake, rapeseed oil cake, kapok oil cake and mustard seed oil cake.

Examples of the animal-based feed are fish meal such as northern ocean meal, imported meal, whole meal and coastal meal, fish soluble, meat meal, meat and bone meal, blood powder, degraded hair, bone meal, treated by-products for livestock, feather meal, silkworm pupa, skim milk, casein and dry whey.

Examples of other feeds are stalks and leaves of plants such as alfalfa, hay cube, alfalfa leaf meal and powder of false acacia, by-products from the corn processing industry such as corn gluten, meal, corn gluten feed and corn steep liquor, processed starch products such as starch, products from the fermentation industry such as yeast, beer cake, malt root, alcohol cake and soy sauce cake, agricultural by-products such as processed citrus fruit cake, tofu cake, coffee cake and cocoa cake, cassava, broad bean, guar meal, seaweeds, krill, spirulina, chlorella and minerals.

Examples of the purified products are proteins such as casein and albumin, amino acids, sugars such as starch, cellulose, sucrose and glucose, minerals and vitamins.

The animal feeds of the present invention can also be produced by using granulating methods such as fluidized bed granulation, stirring granulation, extrusion granulation, rolling granulation, air stream granulation, compression molding granulation, disruption granulation, spray granulation and blasting granulation, coating methods such as pan coating, fluidized bed coating and dry coating, plumping methods such as puff drying, excess steam method, foam mat method and microwave heating method and extrusion methods using an extruding granulator or an extruder.

The feed additives of the present invention can be prepared according to methods similar to those mentioned in (a) above with respect to oral preparations. They can be produced, for example, into powder, granules, pellets, tables and various liquid preparations generally by mixing with or dissolving together with other feed additives as required.

The N-acylated hydroxyproline derivative or a salt thereof, and the amino sugar or a salt thereof and/or the glycosaminoglycan or a salt thereof in the animal feeds of the present invention are added so as to be ingested generally in an amount of 0.02–100 mg/kg, preferably 0.2–20 mg/kg, especially preferably 2–10 mg/kg although the amount varies depending upon the form of intake, the kinds of non-human animals to ingest them and the age and the body weight of the non-human animals.

The animal feeds are fed once or in several parts a day. It is also possible to administer the feed additives of the present invention as an oral preparation for the prevention or the treatment of arthritis for non-human animals in the same dose and for the same period as in the case of the feeds described above.

There is no restriction as to the period for which the feeds are to be given, as it varies depending upon the non-human animal to ingest them. Usually, the period is one week to 5 years, preferably 2 weeks to 2 years.

As in the case of the pharmaceutical of the present invention, the animal feeds of the present invention may be produced so that the N-acylated hydroxyproline derivative or a salt thereof, and the amino sugar or a salt thereof and/or the glycosaminoglycan or a salt thereof are contained in the same animal feed. They may also be produced as a set of feeds.

Examples of the combination of the set of feeds are a combination of an animal feed comprising the N-acylated hydroxyproline derivative or a salt thereof and an animal feed comprising the amino sugar or a salt thereof; a combination of an animal feed comprising the N-acylated hydroxyproline derivative or a salt thereof and an animal feed comprising the glycosaminoglycan or a salt thereof; a combination of an animal feed comprising the N-acylated hydroxyproline derivative or a salt thereof, an animal feed comprising the amino sugar or a salt thereof and an animal feed comprising the glycosaminoglycan or a salt thereof; and a combination of an animal feed comprising the N-acylated hydroxyproline derivative or a salt thereof and an animal feed comprising the amino sugar or a salt thereof and the glycosaminoglycan or a salt thereof, although the combination is not limited thereto.

Each of the animal feeds included in the set may be in any form so long as they exist separately. For example, they may be packed separately or may be present as a mixture in the same container.

In feeding the set of the animal feeds, the feeds may each be fed either simultaneously or separately.

When fed separately, it is desirable that the animal feeds are ingested within the period during which the active ingredients contained in the animal feeds are highly effective in a body. For example, animal feeds are ingested within 8 hours, preferably within 2 hours per one intake.

For the set of animal feeds, the intake is set so that the total intake per day of each active ingredient in the animal feeds corresponds to the above-described daily intake of each ingredient.

Test examples of the present invention are shown below.

Unless otherwise noted, in the following test examples, DBA/1J mice produced by Charles River, powder feed CE2 produced by CLEA Japan, N-acetylhydroxyproline produced by Kyowa Hakko Kogyo, D-glucosamine sulfate 2NaCl as glucosamine (Miyako Kagaku) and chondroitin sodium sulfate (Maruha Kagaku) as chondtoitin were used.

The amounts of the additives in the examples are all shown by weight %.

TEST EXAMPLE 1

Effect of N-acetylhydroxyproline and Glucosamine in Mice with Type II Collagen-Induced Arthritis It is known that arthritis is induced in DBA/1J mice by administering type II collagen two times.

As the first administration of type II collagen, a solution prepared by mixing an equal amount of type II collagen [Collagen Gijutsu Kenshu Kaisha (MCK)] and Freund's complete adjuvant (Iatron) and emulsifying the mixture using a homogenizer was intradermally administered to 6-week old male DBA/1J mice in an amount of 100 µl per one animal.

Twenty-one days after the first administration of type II collagen, EXAMPLE a solution prepared by mixing an equal amount of type II collagen and Freund's complete adjuvant and emulsifying the mixture using a homogenizer in a similar manner was intradermally administered to the animals in an amount of 100 µl per one animal as the second administration of type II collagen. In this manner, arthritis was induced in mice.

Starting on the day of the first administration of type II collagen, the mice were given powder feed CE-2 containing no additive as control; powder feed CE-2 containing 0.1% N-acetylhydroxyproline (indicated as AcHYP in Tables 1-1 and 1-2); powder feed CE-2 containing 0.1% glucosamine (D-glucosamine sulfate 2NaCl); and powder feed CE-2 containing 0.05% N-acetylhydroxyproline and 0.05% glucosamine, respectively. At days 24, 28, 31, 34, 38 and 42 after the first administration of type II collagen, the extent of the development of arthritis was scored according to the following indices.

Scoring was carried out by applying 0–4 points with respect to one of four paws of mice: 0: no symptom; 1: swelling of one finger or swelling (slight) of the ankle; 2: swelling of 1–3 fingers or swelling of the ankle; 3: swelling of 3–5 fingers plus swelling of the ankle; and 4: swelling of all the fingers plus swelling of the ankle. Each mouse was scored the total of the points of 4 paws, namely, 0–16 points.

Twenty mice were subjected to the test with respect to each of the conditions.

The results are shown in Tables 1-1 and 1-2. Table 1-2 is a continuation to Table 1-1.

In the tables, the figures show the scores under different treatment conditions, which are given as mean±SE (N=20).

In the tables, "no treatment" means no administration of type II collagen, and "control" means mice were given the feed containing no additive.

TABLE 1-1

Score of arthritis under various treatment conditions

| Treatment | | Time course (days) | | | |
|---|---|---|---|---|---|
| | | 0 | 24 | 28 | 31 |
| No treatment | | 0.0 ± 0.0 | 0.0 ± 0.0 | 0.0 ± 0.0 | 0.0 ± 0.0 |
| Control | | 0.0 ± 0.0 | 0.1 ± 0.1 | 6.8 ± 0.5 | 10.0 ± 0.6 |
| Glucosamine | 0.1% | 0.0 ± 0.0 | 0.1 ± 0.1 | 5.8 ± 0.6 | 7.7 ± 0.7 |
| AcHYP | 0.1% | 0.0 ± 0.0 | 0.0 ± 0.0 | 6.5 ± 0.7 | 9.5 ± 0.8 |
| AcHYP + Glucosamine | 0.05% 0.05% | 0.0 ± 0.0 | 0.0 ± 0.0 | 4.2 ± 0.7 | 6.9 ± 0.9 |

AcHYP: N-acetylhydroxyproline

TABLE 1-2

Score of arthritis under various treatment conditions
(Continued from Table 1-1)

| Treatment | | 34 | 38 | 42 |
|---|---|---|---|---|
| | | Time course (days) | | |
| No treatment | | 0.0 ± 0.0 | 0.0 ± 0.0 | 0.0 ± 0.0 |
| Control | | 11.0 ± 0.6 | 11.0 ± 0.6 | 10.8 ± 0.6 |
| Glucosamine | 0.1% | 9.2 ± 0.7 | 9.5 ± 0.6 | 9.4 ± 0.6 |
| AcHYP | 0.1% | 10.7 ± 0.8 | 10.8 ± 0.8 | 10.6 ± 0.8 |
| AcHYP + Glucosamine | 0.05% 0.05% | 8.1 ± 1.0 | 8.5 ± 0.9 | 8.5 ± 1.0 |

AcHYP: N-acetylhydroxyproline

As shown in Tables 1-1 and 1-2, lowering of the scores was observed in the case where 0.1% glucosamine or 0.1% N-acetylhydroxyproline was added to the feed compared with the case where no additive was added to the feed (control).

Furthermore, prominent lowering of the scores was observed in the case where 0.05% each glucosamine and N-acetylhydroxyproline are added to the feed compared with the case where 0.1% glucosamine or 0.1% N-acetylhydroxyproline was added.

TEST EXAMPLE 2

Effect of N-acetylhydroxyproline and Chondroitin in Mice with Type II Collagen-Induced Arthritis An experiment similar to that of Test Example 1 was carried out except that chondroitin was used in place of glucosamine.

That is, 21 days after the first administration of type II collagen, a solution prepared by mixing an equal amount of type II collagen and Freund's complete adjuvant and emulsifying the mixture using a homogenizer in a similar manner as in Test Example 1 was intradermally administered to the mice in an amount of 100 μl per one animal as the second administration of type II collagen. In this manner, arthritis was induced in mice.

Starting on the day of the first administration of type II collagen, the mice were given powder feed CE-2 containing no additive as control; powder feed CE-2 containing 0.1% N-acetylhydroxyproline (indicated as AcHYP in Tables 2-1 and 2-2); powder feed CE-2 containing 0.1% chondroitin; and powder feed CE-2 containing 0.05% N-acetylhydroxyproline and 0.05% chondroitin, respectively. At days 23, 27, 30, 33, 36, 40 and 42 after the first administration of type II collagen, the extent of the development of arthritis was scored according to the indices employed in the above Test Example 1.

Twenty mice were subjected to the test with respect to each of the conditions.

The results are shown in Tables 2-1 and 2-2. Table 2-2 is a continuation to Table 2-1. In the tables, the figures show the scores under different treatment conditions, which are given as mean±SE (N=20).

In the tables, "no treatment" means no administration of type II collagen, and "control" means mice were given the feed containing no additive.

TABLE 2-1

Score of arthritis under various treatment conditions

| Treatment | | 0 | 23 | 27 | 30 |
|---|---|---|---|---|---|
| | | Time course (days) | | | |
| No treatment | | 0.0 ± 0.0 | 0.0 ± 0.0 | 0.0 ± 0.0 | 0.0 ± 0.0 |
| Control | | 0.0 ± 0.0 | 0.0 ± 0.0 | 3.8 ± 0.5 | 8.9 ± 0.7 |
| Chondroitin | 0.1% | 0.0 ± 0.0 | 0.1 ± 0.1 | 3.4 ± 0.6 | 7.8 ± 1.0 |
| AcHYP | 0.1% | 0.0 ± 0.0 | 0.1 ± 0.1 | 3.3 ± 0.7 | 7.0 ± 0.9 |
| AcHYP + Chondroitin | 0.05% 0.05% | 0.0 ± 0.0 | 0.1 ± 0.1 | 2.6 ± 0.5 | 5.9 ± 1.0 |

AcHYP: N-acetylhydroxyproline

TABLE 2-2

Score of arthritis under various treatment conditions
(Continued from Table 2-1)

| Treatment | | 33 | 36 | 40 | 42 |
|---|---|---|---|---|---|
| | | Time course (days) | | | |
| No treatment | | 0.0 ± 0.0 | 0.0 ± 0.0 | 0.0 ± 0.0 | 0.0 ± 0.0 |
| Control | | 9.8 ± 0.8 | 9.8 ± 0.8 | 10.0 ± 0.8 | 10.0 ± 0.8 |
| Chondroitin | 0.1% | 9.1 ± 0.9 | 9.7 ± 0.8 | 9.9 ± 0.8 | 9.8 ± 0.7 |
| AcHYP | 0.1% | 7.8 ± 0.9 | 7.9 ± 1.0 | 8.4 ± 0.9 | 8.8 ± 0.8 |
| AcHYP + Chondroitin | 0.05% 0.05% | 7.4 ± 1.0 | 7.8 ± 0.9 | 7.9 ± 1.0 | 7.9 ± 1.0 |

AcHYP: N-acetylhydroxyproline

As shown in Tables 2-1 and 2-2, in the case where 0.1% N-acetylhydroxyproline was added, lowering of the score was observed at any of the days after day 27 compared with the case where no additive was added to the feed (control).

In the case where 0.1% chondroitin was added to the feed, slight lowering of the score compared with control was observed until day 33, but almost no lowering of the score was observed after day 36.

On the other hand, in the case where 0.05% each chondroitin and N-acetylhydroxyproline were added to the feed, lowering of the score compared with control was observed at any of the days after day 27. The lowering of the score was prominent compared with the cases where 0.1% chondroitin or 0.1% N-acetylhydroxyproline was added alone.

TEST EXAMPLE 3

Effect of N-acetylhydroxyproline, Glucosamine and Chondroitin in Mice with Type II Collagen-Induced Arthritis An experiment similar to that of Test Example 1 was carried out except that glucosamine and chondroitin were used in place of glucosamine.

That is, 21 days after the first administration of type II collagen, a solution prepared by mixing an equal amount of type II collagen and Freund's complete adjuvant and emulsifying the mixture using a homogenizer in a similar manner as in Test Example 1 was intradermally administered to the mice in an amount of 100 μl per one animal as the second administration of type II collagen. In this manner, arthritis was induced in mice.

Starting on the day of the first administration of type II collagen, the mice were given powder feed CE-2 containing no additive as control; powder feed CE-2 containing 0.05% N-acetylhydroxyproline (indicated as AcHYP in Tables 3-1 and 3-2); powder feed CE-2 containing 0.05% N-acetylhydroxyproline and 0.05% chondroitin; and powder feed CE-2 containing 0.05% glucosamine, 0.05% glucosamine and 0.05% chondroitin, respectively. At days 24, 28, 31, 35, 38 and 42 after the first administration of type II collagen, the extent of the development of arthritis was scored according to the indices employed in the above Test Example 1.

Twenty mice were subjected to the test with respect to each of the conditions.

The results are shown in Tables 3-1 and 3-2. Table 3-2 is a continuation to Table 3-1. In the tables, the figures show the scores under different treatment conditions, which are given as mean±SE (N=20).

In the tables, "no treatment" means no administration of type II collagen, and "control" means mice were given the feed containing no additive.

TABLE 3-1

Score of arthritis under various treatment conditions

| Treatment | | Time course (days) | | | |
|---|---|---|---|---|---|
| | | 0 | 24 | 28 | 31 |
| No treatment | | 0.0 ± 0.0 | 0.0 ± 0.0 | 0.0 ± 0.0 | 0.0 ± 0.0 |
| Control | | 0.0 ± 0.0 | 0.2 ± 0.1 | 5.7 ± 0.6 | 9.5 ± 0.7 |
| AcHYP | 0.05% | 0.0 ± 0.0 | 0.2 ± 0.1 | 5.4 ± 0.6 | 8.5 ± 0.7 |
| Chondroitin + | 0.05% | 0.0 ± 0.0 | 0.2 ± 0.1 | 4.5 ± 0.7 | 8.4 ± 0.8 |
| Glucosamine | 0.05% | | | | |
| AcHYP + | 0.05% | 0.0 ± 0.0 | 0.1 ± 0.1 | 4.1 ± 0.5 | 7.3 ± 0.8 |
| Glucosamine + | 0.05% | | | | |
| Chondroitin | 0.05% | | | | |

AcHYP: N-acetylhydroxyproline

TABLE 3-2

Score of arthritis under various treatment conditions (Continued from Table 3-1)

| Treatment | | Time course (days) | | |
|---|---|---|---|---|
| | | 35 | 38 | 42 |
| No treatment | | 0.0 ± 0.0 | 0.0 ± 0.0 | 0.0 ± 0.0 |
| Control | | 9.7 ± 0.7 | 9.8 ± 0.7 | 10.2 ± 0.7 |
| AcHYP | 0.05% | 9.4 ± 0.8 | 9.9 ± 0.8 | 9.4 ± 0.7 |
| Chondroitin + | 0.05% | 9.4 ± 0.8 | 9.7 ± 0.7 | 9.5 ± 0.8 |
| Glucosamine | 0.05% | | | |
| AcHYP + | 0.05% | 8.4 ± 0.8 | 8.4 ± 0.8 | 8.5 ± 0.8 |
| Glucosamine + | 0.05% | | | |
| Chondroitin | 0.05% | | | |

AcHYP: N-acetylhydroxyproline

As shown in Tables 3-1 and 3-2, in the cases where 0.05% N-acetylhydroxyproline was added and where 0.05% each glucosamine and chondroitin were added to the feed, almost no lowering of the scores was observed at any of the days after day 24 compared with the case where no additive was added to the feed (control).

On the other hand, where 0.05% each glucosamine, chondroitin and N-acetylhydroxyproline were added to the feed, lowering of the scores compared with control was observed at any of the days after day 24.

TEST EXAMPLE 4

Effect of N-acetylhydroxyproline and Glucosamine Plus Chondroitin in Mice with Type II Collagen-Induced Arthritis As in Test Example 1, 21 days after the first administration of type II collagen, a solution prepared by mixing an equal amount of type II collagen and Freund's complete adjuvant and emulsifying the mixture using a homogenizer in a similar manner as in Test Example 1 was intradermally administered to the mice in an amount of 100 μl per one animal as the second administration of type II collagen. In this manner, arthritis was induced in mice.

Starting at day 28 after the first administration of type II collagen, the mice were given powder feed CE-2 containing no additive as control; powder feed CE-2 containing 0.1% N-acetylhydroxyproline (indicated as AcHYP in Tables 4-1 and 4-2); powder feed CE-2 containing 0.1% glucosamine; powder feed CE-2 containing 0.05% N-acetylhydroxyproline and 0.05% glucosamine; powder feed CE-2 containing 0.05% glucosamine and 0.05% chondroitin; and powder feed CE-2 containing 0.05% N-acetylhydroxyproline, 0.025% glucosamine and 0.025% chondroitin, respectively. At days 28, 33, 36, 39 and 42 after the first administration of type II collagen, the extent of the development of arthritis was scored according to the indices employed in the above Test Example 1.

Ten mice were subjected to the test with respect to each of the conditions.

The results are shown in Tables 4-1 and 4-2. Table 4-2 is a continuation to Table 4-1. In the tables, the figures show the scores under different treatment conditions, which are given as mean±SE (N=10).

In the tables, "no treatment" means no administration of type II collagen, and "control" means mice were given the feed containing no additive.

TABLE 4-1

Score of arthritis under various treatment conditions

| Treatment | | Time course (days) | | |
|---|---|---|---|---|
| | | 0 | 28 | 33 |
| No treatment | | 0.0 ± 0.0 | 0.0 ± 0.0 | 0.0 ± 0.0 |
| Control | | 0.0 ± 0.0 | 4.5 ± 1.0 | 11.0 ± 1.3 |
| AcHYP | 0.1% | 0.0 ± 0.0 | 4.3 ± 0.9 | 9.8 ± 1.0 |
| Glucosamine | 0.1% | 0.0 ± 0.0 | 4.3 ± 0.9 | 9.8 ± 1.2 |
| AcHYP + | 0.05% | 0.0 ± 0.0 | 4.2 ± 0.7 | 8.7 ± 1.0 |
| Glucosamine | 0.05% | | | |
| Glucosamine + | 0.05% | 0.0 ± 0.0 | 4.3 ± 1.3 | 9.3 ± 1.3 |
| Chondroitin | 0.05% | | | |
| AcHYP + | 0.05% | 0.0 ± 0.0 | 4.0 ± 0.9 | 8.7 ± 1.2 |
| Glucosamine + | 0.025% | | | |
| Chondroitin | 0.025% | | | |

AcHYP: N-acetylhydroxyproline

TABLE 4-2

Score of arthritis under various treatment conditions (Continued from Table 4-1)

| Treatment | | Time course (days) | | |
|---|---|---|---|---|
| | | 36 | 39 | 42 |
| No treatment | | 0.0 ± 0.0 | 0.0 ± 0.0 | 0.0 ± 0.0 |
| Control | | 11.4 ± 1.4 | 11.8 ± 1.3 | 11.5 ± 1.4 |
| AcHYP | 0.1% | 10.9 ± 1.1 | 10.7 ± 1.1 | 10.8 ± 1.0 |
| Glucosamine | 0.1% | 10.1 ± 1.1 | 10.4 ± 1.0 | 10.6 ± 1.0 |
| AcHYP + | 0.05% | 10.0 ± 1.0 | 9.5 ± 0.9 | 9.9 ± 1.0 |
| Glucosamine | 0.05% | | | |
| Glucosamine + | 0.05% | 10.0 ± 1.4 | 10.9 ± 1.3 | 10.7 ± 1.2 |
| Chondroitin | 0.05% | | | |
| AcHYP + | 0.05% | 9.2 ± 1.4 | 9.4 ± 1.4 | 9.7 ± 1.3 |
| Glucosamine + | 0.025% | | | |
| Chondroitin | 0.025% | | | |

AcHYP: N-acetylhydroxyproline

As shown in Tables 4-1 and 4-2, in the cases where 0.1% N-acetylhydroxyproline was added and where 0.1% glucosamine was added to the feed, slight lowering of the scores compared with control was observed at any of the days after day 33.

In the case where 0.05% each glucoseamine and chondroitin were added to the feed, slight lowering of the scores compared with control was observed at any of the days after day 33.

On the other hand, in the cases where 0.05% N-acetylhydroxyproline and 0.05% glucosamine were added to the feed and where 0.05% N-acetylhydroxyproline, 0.025% glucosamine and 0.025% chondroitin were added to the feed, lowering of the scores was prominent compared with control at any of the days after day 33.

Examples of the present invention are shown below.

Best Modes for Carrying out the Invetion

Unless otherwise noted, in the following examples, N-acetylhydroxyproline produced by Kyowa Hakko Kogyo, D-glucosamine sulfate 2NaCl as glucosamine (Miyako kagaku) and chondroitin sodium sulfate (Maruha Kagaku) as chondtoitin were used.

EXAMPLE 1

Tablets of 8 mm in diameter and 200 mg in weight each are prepared by mixing the ingredients according to the composition shown in Table 5 below and tableting the resulting mixture using a tableting machine (Hata Seisakusho, HT-AP15SS-U).

TABLE 5

| Composition | Mixing rate (wt %) |
|---|---|
| N-Acetylhydroxyproline | 20 |
| Glucosamine | 10 |
| Lactose | 30 |
| Calcium lactate | 10 |
| Magnesium stearate | 25 |
| Calcium carbonate | 5 |

EXAMPLE 2

Tablets of 8 mm in diameter and 200 mg in weight each were prepared by mixing the ingredients according to the composition shown in Table 6 below and tableting the resulting mixture using a tableting machine (Hata Seisakusho, HT-AP15SS-U).

TABLE 6

| Composition | Mixing rate (wt %) |
|---|---|
| N-Acetylhydroxyproline | 20 |
| Glucosamine | 20 |
| Lactose | 20 |
| Calcium lactate | 10 |
| Magnesium stearate | 25 |
| Calcium carbonate | 5 |

EXAMPLE 3

Tablets of 8 mm in diameter and 200 mg in weight each were prepared by mixing the ingredients according to the composition shown in Table 7 below and tableting the resulting mixture using a tableting machine (Hata Seisakusho, HT-AP15SS-U).

TABLE 7

| Composition | Mixing rate (wt %) |
|---|---|
| N-Acetylhydroxyproline | 15 |
| Glucosamine | 15 |
| Chondroitin | 15 |
| Lactose | 15 |
| Calcium lactate | 10 |
| Magnesium stearate | 25 |
| Calcium carbonate | 5 |

EXAMPLE 4

Tablets of 8 mm in diameter and 200 mg in weight each were prepared by mixing the ingredients according to the composition shown in Table 8 below and tableting the resulting mixture using a tableting machine (Hata Seisakusho, HT-AP15SS-U).

TABLE 8

| Composition | Mixing rate (wt %) |
|---|---|
| N-Acetylhydroxyproline | 20 |
| Chondroitin | 20 |
| Lactose | 20 |
| Calcium lactate | 10 |
| Magnesium stearate | 25 |
| Calcium carbonate | 5 |

EXAMPLE 5

A dog food is prepared according to the composition shown in Table 9.

TABLE 10

| Composition | Content (g) |
|---|---|
| N-Acetylhydroxyplorine | 30 |
| Chondroitin | 10 |
| Pinedex #3 (Matsutani Chemical Industry) | 49 |
| Ferric pyrophosphate (iron source) | 0.1 |
| Phoscal EF (Calcium source: Nikko Fine Products) | 1.0 |
| Vitamin mixture (Merck) | 1.0 |

The above mixture (20 g) is dispersed in 180 ml of water to prepare a drink.

EXAMPLE 7

A soft drink (10 bottles) is prepared from the ingredients shown in Table 11 below.

TABLE 11

| Composition | Content (g) |
|---|---|
| N-Acetylhydroxyproline | 30 |
| Chondroitin | 10 |
| Vitamin C | 1 |
| Vitamin $B_1$ | 0.005 |
| Vitamin $B_2$ | 0.01 |
| Vitamin $B_6$ | 0.025 |
| Liquid sugar | 150 |
| Citric acid | 3 |
| Flavor | 1 |

Water is added to make the volume of 1000 ml.

EXAMPLE 8

A tea drink (1000 ml) is prepared by extracting the ingredients shown in Table 12 below with 1000 ml of water.

TABLE 9

| Composition | Mixing rate (wt %) |
|---|---|
| N-Acetylhydroxyproline | 0.5 |
| Glucosamine | 0.5 |
| Meat meal | 35.0 |
| Corn starch | 40.0 |
| Chicken extract | 5.0 |
| Yeast extract | 5.0 |
| Vegetable oil and fat | 5.0 |
| Calcium lactate | 1.0 |
| Sodium chloride | 1.0 |
| Sodium hydrogenphosphate | 0.5 |
| Magnesium carbonate | 0.5 |
| Ferrous sulfate | 0.1 |
| Vitamin $B_1$ | 0.0005 |
| Vitamin $B_2$ | 0.0005 |
| Vitamin E | 0.001 |
| Niacin | 0.005 |
| Vitamin A | 2000 IU |
| Vitamin D | 150 IU |
| Moisture | 6.3 |

EXAMPLE 6

A drink is prepared from the ingredients shown in Table 10 below.

TABLE 12

| Composition | Content (g) |
|---|---|
| N-Acetylhydroxyproline | 30 |
| Chondroitin | 10 |
| Tea leaves | 15 |

EXAMPLE 9

Cookies (30 pieces) are prepared from the ingredients shown in Table 13 below according to a conventional method.

TABLE 13

| Composition | Content (g) |
|---|---|
| N-Acetylhydroxyproline | 10 |
| Glucosamine | 10 |
| Chondroitin | 10 |
| Soft flour | 100 |
| Starch | 74 |
| Water | 14 |
| Baking powder | 2 teaspoonfuls |
| Salt | ½ teaspoonful |
| Egg | one |
| Butter | 80 |
| Milk | 2 tablespoonfuls |
| Honey | small amount |

EXAMPLE 10

A loaf of bread (4 pounds) is prepared from the ingredients shown in Table 14 below according to a conventional method.

TABLE 14

| Composition | Content (g) |
|---|---|
| N-Acetylhydroxyproline | 15 |
| Glucosamine | 15 |
| Strong flour | 1000 |
| Sugar | 50 |
| Salt | 20 |
| Skim milk | 20 |
| Shortening | 60 |
| Yeast (fresh) | 30 |
| Yeast food | 1 |
| Water | 650 |

EXAMPLE 11

Chewing gum (30 pieces) is prepared from the ingredients shown in Table 15 below according to a conventional method.

TABLE 15

| Composition | Content (g) |
|---|---|
| N-Acetylhydroxyproline | 1 |
| Glucosamine | 1 |
| Gum base | 25 |
| Sugar | 63 |
| Starch syrup | 10 |
| Flavor | 1 |

EXAMPLE 12

Candies (20 pieces) are prepared from the ingredients shown in Table 16 below according to a conventional method.

TABLE 16

| Composition | Content (g) |
|---|---|
| N-Acetylhydroxyproline | 1 |
| Glucosamine | 1 |
| Sugar | 80 |
| Starch syrup | 20 |
| Flavor | 0.1 |

EXAMPLE 13

Marmalade is prepared from the ingredients shown in Table 17 below according to a conventional method.

TABLE 17

| Composition | Content (g) |
|---|---|
| N-Acetylhydroxyproline | 5 |
| Chondroitin | 5 |
| Summer orange peel | 500 |
| Sugar | 200 |
| Summer orange juice | squeezed from one orange |

EXAMPLE 14

Hard capsules (360 mg/capsule) are prepared from the ingredients shown in Table 18 below according to the following method.

TABLE 18

| Composition | |
|---|---|
| N-Acetylhydroxyproline | 250 |
| Glucosamine | 250 |
| Lactose | 60 |
| Corn starch | 30 |
| Hydroxypropyl cellulose | 20 |

N-Acetylhydroxyproline (250 mg) and 250 mg of glucosamine are mixed with 60 mg of lactose and 30 mg of corn starch, to which an aqueous solution of 20 mg of hydroxypropyl cellulose is added. The mixture is kneaded and then granulated according to a conventional method using an extruding granulator. The resulting granules are packed in gelatin hard capsules.

EXAMPLE 15

Soft capsules (170 mg/capsule) are prepared from the ingredients shown in Table 19 below according to the following method.

TABLE 19

| Composition | Content (mg) |
|---|---|
| N-Acetylhydroxyproline | 25 |
| Glucosamine | 25 |
| Soybean oil | 120 |

N-Acetylhydroxyproline (25 mg) and 25 mg of glucosamine are mixed with 120 mg of soybean oil. The mixture is packed in soft capsules according to a conventional method using a rotary dies automatic molding machine.

EXAMPLE 16

Tablets of 8 mm in diameter and 200 mg in weight each are prepared by mixing the ingredients according to the composition shown in Table 20 below and tableting the resulting mixture using a tableting machine (Hata Seisakusho, HT-AP15SS-U).

TABLE 20

| Composition | Mixing rate (wt %) |
|---|---|
| N-Acetylhydroxyproline | 20 |
| Lactose | 40 |
| Calcium lactate | 10 |
| Magnesium stearate | 25 |
| Calcium carbonate | 5 |

On the other hand, tablets of 8 mm in diameter and 200 mg in weight each are prepared by mixing the ingredients according to the composition shown in Table 21 below and tableting the resulting mixture using a tableting machine (Hata Seisakusho, HT-AP15SS-U).

TABLE 21

| Composition | Mixing rate (wt %) |
|---|---|
| Glucosamine | 20 |
| Lactose | 40 |

TABLE 21-continued

| Composition | Mixing rate (wt %) |
|---|---|
| Calcium lactate | 10 |
| Magnesium stearate | 25 |
| Calcium carbonate | 5 |

Furthermore, tablets of 8 mm in diameter and 200 mg in weight each are prepared by mixing the ingredients according to the composition shown in Table 22 below and tableting the resulting mixture using a tableting machine (Hata Seisakusho, HT-AP15SS-U).

TABLE 22

| Composition | Mixing rate (wt %) |
|---|---|
| Chondroitin | 20 |
| Lactose | 40 |
| Calcium lactate | 10 |
| Magnesium stearate | 25 |
| Calcium carbonate | 5 |

These tablets are packed in separate plastic containers together with silica gel, respectively and tightly sealed. These plastic containers are packed in the same paper box.

INDUSTRIAL APPLICABILITY

According to the present invention, it is possible to provide a pharmaceutical, a food and drink, a food additive, an animal feed and a feed additive that have an effect on the prevention or the treatment of arthritis, and a method for preventing or treating arthritis in humans or non-human animals using them.

The invention claimed is:

1. A pharmaceutical composition which comprises an N-acylated hydroxyproline derivative or a salt thereof, an amino sugar or a salt thereof, and a glycosaminoglycan or a salt thereof.

2. The pharmaceutical composition according to claim 1, wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

3. The pharmaceutical composition according to claim 1 or 2, wherein the acyl moiety of said N-acylated hydroxyproline derivative is an acyl group having 2–23 carbon atoms.

4. The pharmaceutical composition according to claim 3, wherein said N-acylated hydroxyproline derivative is N-acetylhydroxyproline.

5. The pharmaceutical composition according to claim 4, wherein said amino sugar is glucosamine or a salt thereof.

6. The pharmaceutical composition according to claim 5, comprising said glycosaminoglycan or salt thereof, wherein said glycosaminoglycan is chondroitin sulfate or a salt thereof.

7. A method for treating arthritis, comprising administering the pharmaceutical composition according to claim 6 to a patient in need thereof.

8. The method according to claim 7, wherein said arthritis is rheumatoid arthritis.

9. A food, drink or an animal feed which comprises an N-acylated hydroxyproline derivative or a salt thereof, an amino sugar or a salt thereof, and a glycosaminoglycan or a salt thereof.

10. The food, drink or the animal feed according to claim 9, wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

11. The food, drink or the animal feed according to claim 9 or 10, wherein the acyl moiety of said N-acylated hydroxyproline derivative is an acyl group having 2–23 carbon atoms.

12. The food, drink or the animal feed according to claim 11, wherein said N-acylated hydroxyproline derivative is N-acetylhydroxyproline.

13. The food, drink or the animal feed according to claim 12, wherein said amino sugar is glucosamine or a salt thereof.

14. The food, drink or the animal feed according to claim 13, wherein said glycosaminoglycan is chondroitin sulfate or a salt thereof.

15. A method for treating arthritis in mammals, which comprises administering a composition comprising (I) and (II):
  (I) an-N-acylated hydroxyproline derivative or a salt thereof,
  (II) at least one of
    (i) an amino sugar or a salt thereof, and
    (ii) a glycosaminoglycan or a salt thereof
to a patient in need thereof.

16. The method according to claim 15 wherein the patient is a human.

17. The method according to claim 15 or 16 wherein said composition is administered orally.

18. The method according to claim 15 or 16, wherein said composition comprises both (i) said amino sugar or salt thereof and (ii) said glycosaminoglycan or salt thereof.

19. The method according to claim 17, wherein said composition comprises both (i) said amino sugar or salt thereof and (ii) said glycosaminoglycan or salt thereof.

* * * * *